(12) United States Patent
Bermudes

(10) Patent No.: US 9,365,625 B1
(45) Date of Patent: *Jun. 14, 2016

(54) BACTERIAL METHIONINE ANALOGUE AND METHIONINE SYNTHESIS INHIBITOR ANTICANCER, ANTIINFECTIVE AND CORONARY HEART DISEASE PROTECTIVE MICROCINS AND METHODS OF TREATMENT THEREWITH

(71) Applicant: David Gordon Bermudes, Woodland Hills, CA (US)

(72) Inventor: David Gordon Bermudes, Woodland Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/954,542

(22) Filed: Nov. 30, 2015

Related U.S. Application Data

(63) Continuation of application No. 13/433,589, filed on Mar. 29, 2012, now Pat. No. 9,200,251.

(60) Provisional application No. 61/470,446, filed on Mar. 31, 2011.

(51) Int. Cl.
| | |
|---|---|
| A01N 63/00 | (2006.01) |
| C12N 1/20 | (2006.01) |
| C12N 15/63 | (2006.01) |
| G01N 33/569 | (2006.01) |
| C07K 14/245 | (2006.01) |
| A61K 38/51 | (2006.01) |
| A61K 38/16 | (2006.01) |

(52) U.S. Cl.
CPC ............. *C07K 14/245* (2013.01); *A61K 38/164* (2013.01); *A61K 38/51* (2013.01)

(58) Field of Classification Search
None
See application file for complete search history.

(56) References Cited

U.S. PATENT DOCUMENTS

| | | | |
|---|---|---|---|
| 4,861,754 | A | 8/1989 | Farkas-Himsley |
| 4,897,348 | A | 1/1990 | Johnson et al. |
| 4,980,163 | A | 12/1990 | Blackburn et al. |
| 5,026,639 | A | 6/1991 | Johnson |
| 5,164,304 | A | 11/1992 | Johnson et al. |
| 5,187,075 | A | 2/1993 | Green et al. |
| 5,217,950 | A | 6/1993 | Blackburn et al. |
| 5,258,289 | A | 11/1993 | Davis et al. |
| 5,260,271 | A | 11/1993 | Blackburn et al. |
| 5,338,664 | A | 8/1994 | Tuckman et al. |
| 5,348,881 | A | 9/1994 | Vedamuthu et al. |
| 5,368,845 | A | 11/1994 | Gaffar et al. |
| 5,451,369 | A | 9/1995 | Daeschel et al. |
| 5,549,895 | A | 8/1996 | Lyon et al. |
| 5,559,096 | A | 9/1996 | Edwards et al. |
| 5,573,797 | A | 11/1996 | Wilhoit |
| 5,573,800 | A | 11/1996 | Wilhoit |
| 5,573,801 | A | 11/1996 | Wilhoit |
| 5,583,013 | A | 12/1996 | Itakura et al. |
| 5,602,021 | A | 2/1997 | Davis et al. |
| 5,668,173 | A | 9/1997 | Garrow |
| 5,691,301 | A | 11/1997 | Blackburn et al. |
| 5,747,309 | A | 5/1998 | Allan et al. |
| 5,753,614 | A | 5/1998 | Blackburn et al. |
| 5,763,395 | A | 6/1998 | Blackburn et al. |
| 5,821,119 | A | 10/1998 | Hagiwara et al. |
| 5,840,281 | A | 11/1998 | Gaffar et al. |
| 5,843,702 | A | 12/1998 | McConnell et al. |
| 5,981,473 | A | 11/1999 | Barefoot et al. |
| 6,020,206 | A | 2/2000 | Vargeese et al. |
| 6,221,847 | B1 | 4/2001 | Barefoot et al. |
| 6,297,371 | B1 | 10/2001 | Colpan et al. |
| 6,306,619 | B1 | 10/2001 | Jones et al. |
| 6,392,119 | B1 | 5/2002 | Gutterson et al. |
| 6,846,484 | B2 | 1/2005 | Vallera et al. |
| 6,942,993 | B2 | 9/2005 | Qiu |
| 7,034,113 | B2 | 4/2006 | Olstein et al. |
| 7,109,322 | B2 | 9/2006 | Colpan et al. |
| 7,112,323 | B2 | 9/2006 | Ibrahim et al. |
| 7,186,545 | B2 | 3/2007 | Collins et al. |
| 7,348,408 | B2 | 3/2008 | Gokce et al. |

(Continued)

FOREIGN PATENT DOCUMENTS

| | | |
|---|---|---|
| WO | WO9411535 | 5/1994 |
| WO | WO9640284 | 12/1996 |

(Continued)

OTHER PUBLICATIONS

Al-Tememy, Waleed KM, et al. "Isolation of *Lactobacillus salivarius* from children and purification of bacteriocin to inhibition cancer cell in vitro." International Journal on Advanced Science, Engineering and Information Technology 1.1 (2011): 104-108.

(Continued)

*Primary Examiner* — Amber D Steele
*Assistant Examiner* — Schuyler Milton
(74) *Attorney, Agent, or Firm* — Steven M. Hoffberg; Ostolenk Faber LLP

(57) ABSTRACT

A substantially purified substance having the properties of a bacterial microcin methionine analog, methionine synthesis inhibitor, tRNA-methionine synthase inhibitors or methionine competitive inhibitor capable of inhibiting tumor cell growth without inhibiting the growth of normal cells or treating neoplastic diseases, and may be used alone or in combination with other anti-cancer agents. The purified substance may also have anti-hyperhomocysteineuria and/or anti-infective properties, such as antifungal activity. The purified substance can be safely administered to animals including humans for the treatment of neoplastic, hyperhomocysteinemia and/or infectious diseases for the treatment of those diseases.

20 Claims, No Drawings

(56) References Cited

U.S. PATENT DOCUMENTS

| | | |
|---|---|---|
| 7,368,235 B2 | 5/2008 | Brem et al. |
| 7,442,762 B2 | 10/2008 | Severinov et al. |
| 7,510,826 B2 | 3/2009 | Colpan et al. |
| 7,592,159 B2 | 9/2009 | Stahl |
| 7,655,775 B2 | 2/2010 | Stiles et al. |
| 7,915,382 B2 | 3/2011 | Qiu |
| 7,935,512 B2 | 5/2011 | Krause et al. |
| 8,062,633 B2 | 11/2011 | Schobitz Twele et al. |
| 8,241,623 B1 | 8/2012 | Bermudes |
| 8,298,758 B2 | 10/2012 | Horikoshi et al. |
| 8,367,066 B2 | 2/2013 | Qiu |
| 8,383,102 B2 | 2/2013 | Donovan |
| 8,415,289 B2 | 4/2013 | Margolis et al. |
| 8,470,583 B1 | 6/2013 | Liu et al. |
| 8,481,045 B2 | 7/2013 | Swartz et al. |
| 8,524,220 B1 | 9/2013 | Bermudes |
| 8,563,293 B2 | 10/2013 | Worthington |
| 8,563,503 B2 | 10/2013 | Qiu |
| 8,568,714 B2 | 10/2013 | Donovan et al. |
| 8,609,110 B2 | 12/2013 | Shanks et al. |
| 8,623,350 B1 | 1/2014 | Bermudes |
| 8,652,806 B2 | 2/2014 | Qiu |
| 8,663,916 B2 | 3/2014 | Qiu |
| 8,673,291 B2 | 3/2014 | Scholl et al. |
| 8,697,640 B2 | 4/2014 | Qiu |
| 8,722,050 B2 | 5/2014 | Qiu |
| 8,771,669 B1 | 7/2014 | Bermudes |
| 8,802,397 B2 | 8/2014 | Qiu |
| 8,802,837 B2 | 8/2014 | Qiu |
| 8,852,917 B2 | 10/2014 | Hill et al. |
| 8,883,161 B2 | 11/2014 | Qiu |
| 9,057,059 B2 | 6/2015 | Grallert et al. |
| 9,068,187 B1 | 6/2015 | Bermudes |
| 9,073,989 B2 | 7/2015 | Qiu |
| 9,139,622 B2 | 9/2015 | Shanks et al. |
| 9,200,251 B1 | 12/2015 | Bermudes |
| 9,200,289 B1 | 12/2015 | Bermudes |
| 2002/0155997 A1 | 10/2002 | Zimmermann et al. |
| 2003/0036175 A1 | 2/2003 | Colpan et al. |
| 2003/0064931 A1 | 4/2003 | Gallivan |
| 2003/0078207 A1 | 4/2003 | Qiu |
| 2003/0124147 A1 | 7/2003 | Vallera et al. |
| 2003/0166266 A1 | 9/2003 | Rombel et al. |
| 2003/0215421 A1 | 11/2003 | McDonald et al. |
| 2004/0005695 A1 | 1/2004 | Miksch et al. |
| 2004/0121939 A1 | 6/2004 | Diana |
| 2004/0142379 A1 | 7/2004 | St. Hilaire et al. |
| 2004/0180094 A1 | 9/2004 | Joyce |
| 2004/0234987 A1 | 11/2004 | Brem et al. |
| 2005/0130269 A1 | 6/2005 | Gokce et al. |
| 2005/0153872 A1 | 7/2005 | Qiu |
| 2005/0245448 A1 | 11/2005 | Vallera et al. |
| 2005/0266512 A1 | 12/2005 | Buckley |
| 2006/0003454 A1 | 1/2006 | Suzuki et al. |
| 2006/0018879 A1 | 1/2006 | Stiles et al. |
| 2006/0037087 A1 | 2/2006 | van Belkum et al. |
| 2006/0154338 A1 | 7/2006 | Stahl |
| 2006/0193867 A1 | 8/2006 | Qiu |
| 2006/0198820 A1 | 9/2006 | McDonald et al. |
| 2006/0229244 A1 | 10/2006 | Dorit et al. |
| 2006/0233813 A1 | 10/2006 | Qiu |
| 2006/0264370 A1 | 11/2006 | Qiu |
| 2006/0270040 A1 | 11/2006 | Filutowicz et al. |
| 2007/0243604 A1 | 10/2007 | Machida et al. |
| 2008/0152759 A1 | 6/2008 | Hong et al. |
| 2008/0233086 A1 | 9/2008 | Stiles et al. |
| 2008/0300169 A1 | 12/2008 | Stahl |
| 2009/0075333 A1 | 3/2009 | Campbell et al. |
| 2009/0092578 A1 | 4/2009 | Su et al. |
| 2009/0233343 A1 | 9/2009 | Kleanthous et al. |
| 2009/0233864 A1 | 9/2009 | Stahl |
| 2009/0324565 A1 | 12/2009 | Krause et al. |
| 2010/0086557 A1 | 4/2010 | Westphal-Daniel et al. |
| 2010/0151097 A1 | 6/2010 | Stahl |
| 2010/0158892 A1 | 6/2010 | Cayley et al. |
| 2010/0184134 A1 | 7/2010 | Voloshin et al. |
| 2010/0184135 A1 | 7/2010 | Voloshin et al. |
| 2011/0293567 A1 | 12/2011 | Eils et al. |
| 2012/0027786 A1 | 2/2012 | Gupta et al. |
| 2012/0088270 A1 | 4/2012 | Qiu |
| 2012/0088717 A1 | 4/2012 | Qiu |
| 2012/0094378 A1 | 4/2012 | Qiu |
| 2012/0121614 A1 | 5/2012 | Vallera et al. |
| 2012/0190826 A1 | 7/2012 | Qiu |
| 2012/0202734 A1 | 8/2012 | Qiu |
| 2012/0208744 A1 | 8/2012 | Postle |
| 2012/0244621 A1 | 9/2012 | Weiss et al. |
| 2012/0277199 A1 | 11/2012 | Ye et al. |
| 2012/0328684 A1 | 12/2012 | Shanks et al. |
| 2013/0066051 A1 | 3/2013 | Qiu |
| 2013/0142797 A1 | 6/2013 | Qiu |
| 2013/0143268 A1 | 6/2013 | Qiu |
| 2013/0143316 A1 | 6/2013 | Qiu |
| 2013/0183685 A1 | 7/2013 | O'Keefe |
| 2014/0073560 A1 | 3/2014 | Shanks et al. |
| 2014/0086835 A1 | 3/2014 | Liu |
| 2014/0090833 A1 | 4/2014 | Weaver et al. |
| 2014/0170170 A1 | 6/2014 | Qiu |
| 2014/0322754 A1 | 10/2014 | Qiu |
| 2014/0349880 A1 | 11/2014 | Qiu |
| 2015/0050311 A1 | 2/2015 | Schubert et al. |
| 2015/0164983 A1 | 6/2015 | Call et al. |
| 2015/0164984 A1 | 6/2015 | Walker et al. |
| 2015/0376604 A1 | 12/2015 | Uppalapati et al. |

FOREIGN PATENT DOCUMENTS

| | | |
|---|---|---|
| WO | WO9907858 | 2/1999 |
| WO | WO0029589 | 5/2000 |
| WO | WO0074686 | 12/2000 |
| WO | WO0100853 | 1/2001 |
| WO | WO0114579 | 3/2001 |
| WO | WO0125397 | 4/2001 |
| WO | WO0151651 | 7/2001 |
| WO | WO03044220 | 5/2003 |
| WO | WO03074554 | 9/2003 |
| WO | WO2004023097 A2 | 3/2004 |
| WO | WO2005000239 A2 | 1/2005 |
| WO | WO2005070014 A2 | 8/2005 |
| WO | WO2008090223 A2 | 7/2008 |
| WO | WO2008155120 A2 | 12/2008 |
| WO | WO2010014943 A2 | 2/2010 |

OTHER PUBLICATIONS

Ballouche, Mathieu, Pierre Cornelis, and Christine Baysse. "Iron metabolism: a promising target for antibacterial strategies." Recent patents on anti-infective drug discovery 4.3 (2009): 190-205.

Balvir, Kumar. "In Vitro cytotoxicity of native and rec-pediocin CP2 against cancer cell lines: a comparative study." Pharmaceutica Analytica Acta (2012).

Baqai, Rakhshanda, and Erum Habib. "Inhibitory Activity of Colicin Producing *Escherichia coli* Isolated from Clinical Specimens." Infectious Diseases Journal of Pakistan: 689, (2014).

Bures, Jan, et al. "Bacteriocinogeny in experimental pigs treated with indomethacin and *Escherichia coli* Nissle." World journal of gastroenterology: WJG 17.5 (2011): 609.

Choi, Jeong-Hae, et al. "The bacterial protein azurin enhances sensitivity of oral squamous carcinoma cells to anticancer drugs" Yonsei medical journal 52.5 (2011): 773-778.

Cursino, Luciana, Edmar Chartone-Souza, and Andréa Nascimento. "Recent updated aspects of colicins of Enterobacteriaceae." Brazilian Journal of Microbiology 333 (2002): 185-195.

Dicks, L. M. T., et al. "Medical and personal care applications of bacteriocins produced by lactic acid bacteria." Prokaryotic Antimicrobial Peptides. Springer New York, 2011. 391-421.

Gillor, Osnat, Lisa M. Nigro, and Margaret A. Riley. "Genetically engineered bacteriocins and their potential as the next generation of antimicrobials." Current pharmaceutical design 11.8 (2005): 1067-1075.

Gilson, L. Y. N. N. E., Hare Khrisna Mahanty, and R. Kolter. "Four plasmid genes are required for colicin V synthesis, export, and immunity." Journal of bacteriology 169.6 (1987): 2466-2470.

(56) References Cited

OTHER PUBLICATIONS

Giri, Samir, and Jitendra Singh. "New Face in the Row of Human Therapeutics: Bacteriocins." Journal of Microbiology Research 3.2 (1926): 71-78.

Hetz, Claudio, et al. "Microcin E492, a channel-forming bacteriocin from *Klebsiella pneumoniae*, induces apoptosis in some human cell lines." Proceedings of the National Academy of Sciences 99.5 (2002): 2696-2701.

Kamarajan, Pachiyappan, et al. "Nisin ZP, a bacteriocin and food preservative, inhibits head and neck cancer tumorigenesis and prolongs survival." PloS one 10.7 (2015): e0131008.

Karpiński, Tomasz M., and Anna K. Szkaradkiewicz. "Characteristic of bacteriocines and their application." Pol J Microbiol 623 (2013): 223-235.

Kaur, Sumanpreet, and Sukhraj Kaur. "Bacteriocins as Potential Anticancer Agents." Frontiers in pharmacology 6 (2015).

Kohoutova, Darina, et al. "*Escherichia coli* strains of phylogenetic group B2 and D and bacteriocin production are associated with advanced colorectal neoplasia." BMC infectious diseases 14.1 (2014): 733.

Kumar, Balvir, et al. "Cloning and expression of bacteriocins of *Pediococcus* spp.: A review." Archives of Clinical Microbiology 2.3 (2011): 4.

Lagos R., et al. "Antibacterial and antitumorigenic properties of microcin E492, a pore-forming bacteriocin." Current pharmaceutical biotechnology 10.1 (2009): 74-85.

López-Meza, Joel E., Alejandra Ochoa-Zarzosa José A. Aguilar, and Pedro D. Loeza-Lara. Antimicrobial peptides: diversity and perspectives for their biomedical application. INTECH Open Access Publisher, 2011.

Mathavan, Indran, et al. "Structural basis for hijacking siderophore receptors by antimicrobial lasso peptides." Nature chemical biology 10.5 (2014): 340-342.

Mosbahi, Khédidja, et al. "The cytotoxic domain of colicin E9 is a channel-forming endonuclease." Nature Structural & Molecular Biology 9.6 (2002): 476-484.

Nascimento, S. "Influence of growth conditions on production of klebicin K and raoultellin L, two antimicrobial substances against Gram-negative pathogens." International Journal of Pharmaceutical & Biological Archive 2.4 (2011).

Nolan, Elizabeth M., et al. "Biosynthetic tailoring of microcin E492m: post-translational modification affords an antibacterial siderophore-peptide conjugate." Journal of the American Chemical Society 129.46 (2007): 14336-14347.

O'Shea, Eileen F., et al. "Production of bioactive substances by intestinal bacteria as a basis for explaining probiotic mechanisms: bacteriocins and conjugated linoleic acid." International journal of food microbiology 152.3 (2012): 189-205.

Oyinloye, Babatunji Emmanuel, Abiola Fatimah Adenowo, and Abidemi Paul Kappo. "Reactive Oxygen Species, Apoptosis, Antimicrobial Peptides and Human Inflammatory Diseases." Pharmaceuticals 8.2 (2015): 151-175.

Riley, Margaret A., and John E. Wertz. "Bacteriocins: evolution, ecology, and application." Annual Reviews in Microbiology 56.1 (2002): 117-137.

Riley, Margaret A. Research and applications in bacteriocins. Horizon Scientific Press, 2007.

San Millá n, J. L., R. Kolter, and F. Moreno. "Evidence that colicin X is microcin B17." Journal of bacteriology 169.6 (1987): 2899-2901.

Sang, Yongming, and Frank Blecha. "Antimicrobial peptides and bacteriocins: alternatives to traditional antibiotics." Animal Health Research Reviews 9.02 (2008): 227-235.

Savadogo, Aly, et al. "Bacteriocins and lactic acid bacteria-a minireview." African Journal of Biotechnology 5.9 (2006).

Shaikh, Faraz, P. A. Abhinand, and P. K. Ragunath. "Identification & Characterization of lactobacillus *Salavarius bacteriocins* and its relevance in cancer therapeutics." Bioinformation 8.13 (2012): 589.

Singh, Jitendra, and C. Ghosh. "Ribosomal encoded bacteriocins: their functional insight and applications." J. Microbiol. Res 2.2 (2012): 19-25.

Urbizu, Lucia, M. Sparo, and S. Sánchez Bruni. "Bacterial antagonist mediated protein molecules." Clin Exp Pharmacol 3.123 (2013): 2161-1459.

Zhang, Li Hong, et al. "Genetic analysis of the colicin V secretion pathway." Genetics 141.1 (1995): 25-32.

Zschüttig, Anke, et al. "Identification and characterization of microcin S, a new antibacterial peptide produced by probiotic *Escherichia coli* G3/10." PLoS One 7.3 (2012).

Zucca, Mario, Dianella Savoia, and Sara Scutera. Antimicrobial peptides: new frontiers in the therapy of infections. INTECH Open Access Publisher, 2011.

BACTERIAL METHIONINE ANALOGUE AND METHIONINE SYNTHESIS INHIBITOR ANTICANCER, ANTIINFECTIVE AND CORONARY HEART DISEASE PROTECTIVE MICROCINS AND METHODS OF TREATMENT THEREWITH

CROSS REFERENCE TO RELATED APPLICATIONS

The present application is a Continuation of U.S. patent application Ser. No. 13/433,589, filed Mar. 29, 2012, now U.S. Pat. No. 9,200,251, issued Dec. 1, 2015, which is a non-provisional of, and claims benefit of priority from, U.S. Provisional Patent Application No. 61/470,446, filed Mar. 31, 2011, each of which is expressly incorporated herein by reference in its entirety.

1. FIELD OF THE INVENTION

The present invention relates to bacterial microcins, methionine analogues, tRNA-methionine synthase inhibitors, and methionine synthesis inhibitors and their pharmaceutical use.

2. BACKGROUND OF THE INVENTION

Citation or identification of any reference herein, or any section of this application shall not be construed as an admission that such reference is available as prior art to the present application. The disclosures of each of these publications and patents are hereby incorporated by reference in their entirety in this application, and shall be treated as if the entirety thereof forms a part of this application.

Microcins are a class of bacteriocin antibacterial products produced by bacteria with the ability to directly or indirectly kill or inhibit other bacterial species (Duquesne et al., 2007, Microcins, gene-encoded antibacterial peptides from enterobacteria, Natural Product Reports, 24: 708-734, Hen and Jack, Chapter 13 Microcins, in Kastin (ed.), 2006, Handbook of Biologically Active Peptides, Academic Press; Alouf and Popoff (eds.), 2006, Comprehensive Sourcebook of Bacterial Protein Toxins, Third Edition, Academic Press). Use of bacteriocins, including colicins and microcins, for the treatment of cancer has previously been suggested (WO 2001/014579; WO 2003/074554). However, the use of methionine analogue or microcin methionine synthesis inhibitors, methionine analogues, derivatives or isomers, or tRNA-methionine synthase inhibitors has not previously been suggested for the treatment of cancer.

Coronary heart disease is associated with elevated levels of homocysteine (hyperhomocysteinemia; Eikelboom et al., 1999, Homocysteine and cardiovascular disease: a critical review of the epidemiologic evidence. Ann Intern Med. 131: 363-375). Homocysteine is a homologue of the amino acid cysteine containing an additional methylene ($-CH_2$) group. It is synthesized from methionine by the removal of the methyl group, and can be reconverted to methionine by re-addition of the methyl group. Treatments for hyperhomocysteinemia include betaine, which enhances the reconversion of homocysteine to methionine. Suggested treatments have also included thetin for enhancing the conversion of homocysteine to methionine (U.S. Pat. No. 5,668,173). Methods for measuring methionine (WO 2005/070014), S-adenosyl-methionine (SAM; WO 2001/051651) cysteine (WO 2003/044220) and homocysteine levels have been described (U.S. Pat. No. 6,020,206; WO 2001/000853; WO 2004/023097) and are known to those skilled in the art. Treatments blocking conversion of methionine to homocysteine using bacterial microcins, methionine analogues, tRNA-methionine synthase inhibitors or methionine synthesis inhibitors have not been previously suggested.

Methionine analogues described by Bassiri and Rahimi-Larijani (WO/201001493) did not include microcins as methionine analogues or inhibitors of methionine metabolism. Bacterial species are known to be susceptible to agents such as bacteriocins including microcins. However, methionine analogue microcins have not been suggested to have broad antiinfective activity. The types of infectious diseases for which methionine analogue microcins are effective may generally include prions, viruses (e.g., hepatitis C), bacteria (e.g., *Staphylococcus aureus, Pseudomonas aeruginosa*), protozoans (e.g., *Entamoeba histolytica, plasmodium falciparum*), fungi (e.g., *Candida albicans, Pneumocystis carnii*) and helminthes (e.g., *Ancylostoma duodenale, Schistosoma mansoni*), (Mandell, Bennett and Dolin 2010, Principles and Practices of Infectious Diseases, $7^{th}$ Edition, Elsevier Publishers, 4320 pages).

3. SUMMARY OF THE INVENTION

3.1 Therapeutic Molecules

The present invention provides pharmaceutical agents for use in treating animals which are, or are derived from, bacterial microcins.

These compositions, for example in pharmaceutical formulations, may be used to treat neoplastic diseases, and coronary heart diseases (CHD). The agents are well tolerated, suppress methionine intolerance in CHD and exhibit toxicity to tumor cells with reduced toxicity to normal cells. The agents may also be used to treat infectious diseases.

These microcins (or related compositions) can be formed synthetically, semi-synthetically, or purified from culture media.

In another embodiment, a microcin, methionine analogue, tRNA-methionine synthase inhibitors or methionine synthesis inhibitor-producing organism, e.g., a genetically engineered organism or a wild type probiotic organism, may itself form part of a therapy (e.g., WO/2008/155120 Methods And Compositions For Treating Mucositis; WO/2008/090223 Treatment Of Immune Disease By Mucosal Delivery Of Antigens Using Genetically Modified *Lactobacillus*; WO/2001/025397 Compositions And Methods For Tumor-Targeted Delivery Of Effector Molecules). Typically, a genetically engineered organism with defined and desirable traits is employed, such as attenuation to avoid unintended pathology, and susceptibility to antibiotics in case eradication is required. A live bacteria may be administered, for example, either systemically (e.g., parenteral, intravenous, intramuscular, intralymphatic, intradermal, subcutaneous) or to the mucosal system through oral, nasal, intravessically or suppository administration. Probiotic bacteria include *Lactobacillus* sp., *Lactococcus* sp., *Leuconostoc* sp., *Pediococcus* sp., *Streptococcus* sp., *Lactococcus* sp., *Bacillus* sp., *Bifidobacterium* sp., *Bacteroides* sp., and *Escherichia coli* such as the 1917 Nissel strain. The probiotic bacteria may also include attenuated pathogenic bacteria such as attenuated *Salmonella typhimurium* (e.g., VNP20009) or other *Salmonella* serotypes, or attenuated *Streptococcus*, such as *S. agalactiae*. Other bacterial strains are also encompassed, including non-pathogenic bacteria of the gut such as *E. coli* strains, *Bacteriodies, Bifidobacterium* and *Bacillus*, attenuated pathogenic strains of *E. coli* including enteropathogenic and uropathogenic isolates, *Enterococcus* sp. and *Serratia* sp. as well as attenuated *Neisseria* sp., *Shigella* sp., *Staphalococcus* sp., *Yersinia* sp., *Streptococcus* sp., and *Listeria* sp. Bacteria of low pathogenic potential to humans such as insect pathogenic *Xenorhabdus* sp., *Photorhabdus* sp. and human wound *Photorhabdus* (*Xenorhabdus*) are also encompassed. It is known to those skilled in the art that minor variations in molecular biology techniques between gram-negative and gram-positive organisms, such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336) are required and substituted as needed.

The present invention also employs, for example, isolated or substantially purified bacterial microcin methionine analogues or methionine synthesis inhibitor introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically, intrathecally, by inhaler or nasal spray) or to the mucosal system through oral, nasal, pulmonary intravesically, enema or suppository administration where they become biologically available and thereby provide a therapeutic benefit by reducing or eliminating the disease, malignancy and/or neoplasia. The level or isolation or purification is dependent on pharmacological acceptability of the respective formulation, and absence of interfering or toxic substances.

The microcins are produced and purified from bacterial cultures by methods known to those skilled in the art for the purification of amino acids, including all forms of chromatography, ion exchange, electrophoresis, differential extractions, precipitations (e.g., Faurie and Thommel (eds) 2003, Microbial production of L-amino acids. Springer; Kumar and Gomes, 2005, Methionine production by fermentation, Biotechnology Advances 23: 41-61). Endotoxin (bacterial lipopolysaccharides; LPS) are removed using methods known to those skilled in the art (US20030036175, U.S. Pat. No. 7,109,322, U.S. Pat. No. 7,510,826, Colpan et al., Process for the depletion or removal of endotoxins; U.S. Pat. No. 6,297,371 Colpan et al., Process for the preparation of endotoxin-free or endotoxin-depleted nucleic acids and/or oligonucleotides for gene therapy, each of which is expressly incorporated herein by reference).

The types of cancers or neoplasias to which the present invention is or may be directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas.

The types of metabolic disorders include those for which methionine plays a central role, including but not limited to hypercysteinemia.

The types of infectious diseases for which methionine analogue or methionine synthesis inhibitor microcins are effective may generally include prions, viruses (e.g., hepatitis C), bacteria (e.g., *Staphylococcus aureus, Pseudomonas aeruginosa*), protozoans (e.g., *Entamoeba histolytica, plasmodium falciparum*), fungi (e.g., *Candida albicans, Pneumocystis carnii*) and helminthes (e.g., *Ancylostoma duodenale, Schistosoma mansoni*), (Mandell, Bennett and Dolin 2010, Principles and Practices of Infectious Diseases, 7$^{th}$ Edition, Elsevier Publishers, 4320 pages).

4. OBJECTS OF THE INVENTION

The present invention provides, according to one embodiment, substantially purified microcins, methionine analogues or methionine synthesis inhibitors that have antineoplastic activity and provide a benefit to a patient with cancer or other forms of neoplastic disease. In a preferred embodiment, the tumor types treated by the microcins, methionine analogues, tRNA-methionine synthase inhibitors or methionine synthesis inhibitors are generally deficient in methylthioadenosine phosphorylase (MTAP). In another embodiment, the microcins, methionine analogues, tRNA-methionine synthase inhibitors or methionine synthesis inhibitors are used as part of a combination chemotherapy. In a preferred embodiment, the methionine analogues or methionine synthesis inhibitor are used in combination with a chemotherapeutic agent. In another preferred embodiment, the microcins, methionine analogues, tRNA-methionine synthase inhibitors or methionine synthesis inhibitors are used in combination with methioninase. In another embodiment, the substantially purified microcins, methionine analogues, tRNA-methionine synthase inhibitors or methionine synthesis inhibitors provide a benefit to a patient with hyperhomocysteinemia by reducing or inhibiting the conversion of homocysteine from methionine. In another embodiment, the microcins, methionine analogues, tRNA-methionine synthase inhibitors or methionine synthesis inhibitors are used for the treatment of infectious diseases. In another embodiment, a pharmaceutical composition comprises a pharmaceutically acceptable carrier and one or more microcin methionine analogs or methionine synthesis inhibitors.

The present invention encompasses, for example, treatment protocols that provide a better therapeutic effect than current existing anticancer therapies. In particular, the present invention provides methods for prophylaxis or treatment of neoplastic diseases in a subject comprising administering to said subject and one or more methionine analogue microcins or methionine synthesis inhibitors. Accordingly, when administered to an individual, a microcins, methionine analogues, tRNA-methionine synthase inhibitors or methionine synthesis inhibitors, in accordance with the present invention, results in anti-neoplastic activity.

The present invention encompasses treatment protocols that provide a better therapeutic effect than current existing anti-hyperhomocysteinemia therapies. In particular, the present invention provides methods for prophylaxis or treatment of hyperhomocysteinemia in a subject comprising administering to said subject and one or more microcins, methionine analogues, tRNA-methionine synthase inhibitors or methionine synthesis inhibitors. Accordingly, when administered to an individual, a microcins, methionine analogues, tRNA-methionine synthase inhibitors or methionine synthesis inhibitors, in accordance with the present invention, results in anti-hyperhomocysteinemia.

It is therefore an object to provide a method of treating an animal, comprising administering an effective dose of at least one pharmaceutically acceptable microcin, methionine analogue or methionine synthesis inhibitor, to an animal having at least one of a tumor, hyperhomocysteinemia, and an infectious disease, to thereby respectively inhibit tumor growth, treat hyperhomocysteinemia, or treat the infectious disease.

It is a further object to provide a method of treating an animal, comprising: determining a presence of a disease selected from the group consisting of a neoplasia, hyperhomocysteinemia, and an infectious disease; administering a regimen of effective doses of a pharmaceutically acceptable composition comprising at least one of isolated microcins, methionine analogues, and or methionine synthesis inhibitors, to an animal having the disease, over a sufficient time to achieve an effective treatment of the disease; and monitoring the treatment by performing at least one laboratory test to determine at least one of a neoplasm size, a homocystiene level, and a presence of an infectious organism.

It is also an object to provide a pharmaceutical composition for administration to a human, comprising at least one pharmaceutically acceptable agent selected from the group consisting of microcins, methionine analogues and methionine synthesis inhibitors, which has been substantially purified, in unit dose form.

The pharmaceutically acceptable microcin, methionine analogue or methionine synthesis inhibitor with tumor growth inhibitory ability may be administered in combination with a microtubule depolymerizing agent. The microtubule inhibitory agent may comprise at least one of vincristine, vinorelbine, vinblatine and mebendazol.

The at least one pharmaceutically acceptable microcin, methionine analogue, or methionine synthesis inhibitor may be administered in combination with methioninase. Methioninase may be concurrently administered during the regimen.

The pharmaceutically acceptable composition may comprise a purified methionine analog microcin, or a purified methionine synthesis inhibitor microcin. The pharmaceutically acceptable microcin, methionine analogue or methionine synthesis inhibitor comprises a microcin which is at least one of (a) derived from *E. coli* LP 136, *E. coli* LP-93 and *E. coli* LP15, D93, N-15, V517; (b) encoded by at least one plasmid selected from the group consisting of plasmid pCP101, pCP102, pCP103, pCP104, pCP105, pCP106, and pVA517C; and (c) microcin 15m.

The animal may have an infectious disease caused by a fungus. The fungus may comprise at least one of *Pneumocystis carnii* and *Candida albicans*.

The animal may have a tumor comprising a neoplasia originating in a tissue selected from the group consisting of stomach, colon, rectum, liver, pancreas, lung, breast, cervix uteri, corpus uteri, ovary, prostate, testis, bladder, kidney, brain, central nervous system, head, neck, throat, or selected from the group consisting of Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney and lymphoma cancer.

The pharmaceutical composition may further comprise a pharmaceutically acceptable excipient, additive or carrier. The unit dose form may comprise an intravenous dosage vial, or an oral unit dosage form, or a parenteral dosage form.

5. DEFINITIONS

In order that the invention may be more fully understood, the following terms are defined.

The phrase "effective amount" is used throughout the specification to describe an amount of the present compound or composition which is used to effect an intended result. In most aspects of the present invention the term effective amount is used in conjunction with the treatment of a patient suffering from neoplasia to prevent the further growth of the neoplasms, to bring that growth under control or even kill cancerous cells and preferably, produce a remission of the tumor. In other aspects of the present invention the term effective amount is used in conjunction with the treatment of a patient suffering from hyperhomocysteinuria to prevent the further conversion of methionine to homocysteine.

The phrase "substantially purified" means a preparation having better than 80% purity, preferably more than 90% pure and more preferably greater than 95% pure, more preferably greater than 97% pure, more preferably greater than 99% pure. Purity in this case refers to compounds having specific biological activity of the desired composition(s), and may comprise a plurality of compositions which together have the desired specific biological activity. The purification is intended to remove contaminants derived from the production process or source, and is not intended to exclude intentionally added or retained components. After purification, the composition may be diluted or otherwise compounded with other active or inactive ingredients.

The term "coadministered" is used to describe the administration of a compound according to the present invention in combination with another drug, to a patient, regardless of the time of administration, such that effective amounts of the present compounds and the coadministered drugs are present in the patient at the same time during therapeutic treatment.

As used herein, the term "analog" or "analogue" refers to a compound that possesses a similar or identical sub-structure as another molecule, such as an amino acid molecule, or to be a competitive inhibitor thereof, but does not necessarily comprise a similar or identical function.

As used herein, the phrase "methionine synthesis inhibitor" refers to a component that may or may not possess similar or identical sub-structure as another molecule, such as an amino acid molecule, or amino acid analogue, but acts to inhibit the synthesis of the similar or identical sub-structure, such as the methionine amino acid.

As used herein, the phrase "unit dose form" refers to a pharmaceutically acceptable formulation packaged or otherwise provided in a form which is appropriate for administration in an integral multiple, or in some instances, a readily generated fraction, for a single patient at a single time. Thus, pills, capsules, single use ampoules, and the like are examples of unit dose forms.

6. DETAILED DESCRIPTION OF THE INVENTION

The present invention provides, according to various embodiments, substantially purified microcins, methionine analogues, tRNA-methionine synthase inhibitors or methionine synthesis inhibitors including homoserine O-succinyltransferase inhibitor therapeutic molecules. In particular, one aspect of the invention relates to treatment of cancer of an individual by eliciting a therapeutic response against cancer. The types of cancer may generally include solid tumors, carcinomas, leukemias, lymphomas and multiple myelomas. In addition, therapeutic microcins, methionine analogues, tRNA-methionine synthase inhibitors or methionine synthesis inhibitors including homoserine O-succinyltransferase inhibitors have enhanced activity when coadministered with methionine-depleting agents such as methioninase. Another aspect of the invention relates treatment of hyperhomocysteinemia by administering microcins, methionine analogues, tRNA-methionine synthase inhibitors or methionine synthesis inhibitors molecules to an individual to elicit a therapeutic response against excessive production of homcysteine from methionine. Another aspect of the invention relates to treatments of infectious diseases. The types of infectious diseases for which methionine analogue microcins are effective may generally include prions, viruses, bacteria, protozoans (protists), fungi (e.g., *Candida albicans, Pneumocystis carnii*) and helminthes (Mandell, Bennett and Dolin 2010, Principles and Practices of Infectious Diseases, 7$^{th}$ Edition, Elsiever Publishers, 4320 pages).

Microcin methionine analogues, methionine-competitive microcins, methionine synthesis inhibitors or isomers thereof including homoserine 0-succinyltransferase inhibitors have been described directly or indirectly as antibacterial bacteriocin with antibacterial properties by several authors (Sanchez et al., 1986, Plasmid pVA517C from *Escherichia coli* V517 is required for the expression of an antibiotic microcin, J. Antbiotics (Tokyo) 39: 1028-1030; Martinez and Perez-Diaz 1990, Cloning the determinants for microcin D93 production and analysis of three different D-type microcin plasmids. Plasmid 23: 216-225; Aguilar et al., 1982, Microcin 15m from *Escherichia coli*: mechanism of antibiotic action, Antimicrobial Agents and Chemotherapy 21: 381-386, inhibits homoserine-O-transsuccinylase; Aguilar et al., 1983, Microcin N-15, a $2^{nd}$ antibiotic from *Escherichia coli* LP15, Journal of Antibiotics 36: 325-327; Aguilar et al., 1982, Mechanisms involved in the increased sensitivity of *Escherichia coli* to microcin 15M at 42 degrees C., Current Microbiol 7: 83-86; Blanco et al., 1986, Effect of growth rate and aeration on the production of microcin by *Escherichia coli* growing in continuous culture, Microbios 46: 59-64; Kurepina and Khmel 1986, Microcins: their nature and genetic determination, Mol. Gen. Mikrobiol Virusol 4: 3-9; Perez-Diaz and Clowes 1980, Physical characterization of plasmids determining synthesis of a microcin which inhibits methionine synthesis in *Escherichia coli*, J. Bacteriology 141: 1015-1023; Martinez and Perez-Diaz 1990, Cloning the determinants for microcin D93 production and analysis of three different D-type microcin plasmids, Plasmid 23: 216-225; Martinez and Perez-Diaz 1986, Isolation, characterization and mode of action on *Escherichia coli* strains of microcin D93, Antimicrobial Agents and Chemotherapy 29: 456-460; Sable et al., 2003, Wild-type *Escherichia coli* producing micrcins B17, D93, J25 and microcin L production and immunity, Can. J. Microbiology 49: 356-361). Methionine analogues, tRNA-methionine synthase inhibitors methionine isomers, methionine synthesis inhibitors including homoserine 0-succinyltransferase inhibitors are produced by several bacterial strains containing microcin plasmids, including but not limited to *E. coli* LP 136, *E. coli* LP-93 and *E. coli* LP15, and are believed to be variously encoded by the plasmids pCP101, pCP102, pCP103, pCP104, pCP105, pCP106, and/or pVA517C. Isolation of new methionine analogue or methionine synthesis inhibitor microcins from animal, human, clinical, or environmental samples can be performed using standard techniques described by the authors above, including diffusion through a cellophane membrane and diminution of effect in the presence of excess methionine.

Methionine dependence is used as a guide for selection of cancerous, metabolic and infectious targets, such as solid tumors, hyperhomocysteinemia, or an infectious disease such as *Pneumocystis*. Methionine dependency has been described by Durando et al., 2008 (Methionine dependency of cancer cells; A new therapeutic approach? Bull Cancer 95: 69-76 and Mecham et al., 1983, The metabolic defect of methionine dependence occurs frequently in human tumor cell lines, Biochem. Biophys. Res. Comm. 117: 429-434) and treatments using methioninase have been described by Miki et al., 2000, Cancer Research 60: 2696-2702; Miki et al., 2000, Cancer Gene Therapy 7: 332-338; Tan et al., 1999 Clin Cancer Res 5: 2157-2163; Yoshido et al., 1998, Cancer research 58: 2583-2587).

For the treatment of cancer, therapeutic methionine microcin analogues are tested for cytotoxicity to cancer cells of different types (e.g., colon, lung, breast, prostate, stomach) and different genetic backgrounds (e.g., p53). The microcins, methionine analogues, tRNA-methionine synthase inhibitors or methionine synthesis inhibitors including homoserine O-succinyltransferase inhibitors may also be tested for effects on cancer cell signaling pathways (Adjei and Hidalgo 2005, Intracellular signal transduction pathway proteins as targets for cancer therapy, J. Clin Oncology 23: 5386-5403) and genotoxic stress pathways (Newton et al., 2004, The utility of DNA microarrays for characterizing genotoxicity, Environmental Health Perspectives 112: 420-422), and cross-referenced with the genetic background and tumor cell type. The effect of the microcins, methionine analogues, tRNA-methionine synthase inhibitors or methionine synthesis inhibitors on in vitro cytotoxicity is determined using standard cell culture techniques and cytotoxicity assays such as MTT (3-(4,5-Dimethylthiazol-2-yl)-2,5-diphenyltetrazolium bromide, a tetrazol; Mosmann 1983; J. Immunol Methods 65:55-63) known to those skilled in the art. The contribution of the microcins, methionine analogues, tRNA-methionine synthase inhibitors or methionine synthesis inhibitors and cytotoxic agents or methioninase are determined individually and in combination. Methioninase (methionine gamma-lyase) treatments have been previously described (WO 2000/029589; WO 1999/007858; WO 1996/040284; WO 1994/011535). Combination effects, including antagonism, additivity or synergy may determined using the median effect analysis (Chou and Talaly 1981 Eur. J. Biochem. 115: 207-216) or other standard methods (White et al., 1996, Antimicrobial Agents and Chemotherapy 40: 1914-1918; Brenner, 2002, Annals of Oncology 13: 1697-1698; Berenbaum M C. 1989. What is synergy? Pharmacol Rev. 41(2): 93-141; Greco W R, Bravo G, Parsons J C. 1995. The search for synergy: a critical review from a response surface perspective. Pharmacol Rev. 47(2): 331-85); Zhao et al., 2004, Evaluation of Combination Chemotherpy, Clin Cancer Res 10: 7994-8004; Loewe and Muischnek, 1926. Effect of combinations: mathematical basis of the problem, Arch. Exp. Pathol. Pharmakol. 114: 313-326). The assay may also be used to determine synergy, additivity or antagonism of two or more bacterial methionine analogue microcins. The assay may also be used to determine synergy, additivity or antagonism a bacterial methionine analogue microcins together with microtubule depolymerizing agents (vincristine, vinorelbine, vinblatine and mebendazole) conventional small molecule cytotoxin (e.g., cisplatin, doxorubicin, irinotecan, paclitaxel; Chu and DeVita, 2010, Physicians' Cancer Chemotherapy Handbook, Jones and Bartlett), targeted therapeutic (e.g., imatinib, irissa, cetuximab), proteosome inhibitors (e.g., bortezomib), mTOR inhibitors or PARP inhibitors. In vivo studies (G. K. Schwartz (ed) 2005, Combination cancer therapy: Modulators and potentiators, Human Press, Totowa, N.J., 284 pp.; B. A. Teicher and P. A. Andrews (eds.) 2004, Anticancer drug development guide, Preclinical screening, clinical trials and approval, Second Edition, Humana Press, Totowa, N.J., 450 p.; Teicher (ed.) 2002, Tumor models in cancer research, Human Press, Totowa, N.J., 690 p) may also be performed with antiangiogenic inhibitors such as Avastin, combrettastatin, thalidomide.

For the treatment of hyperhomocysteinemia, therapeutic microcins, methionine analogues, tRNA-methionine synthase inhibitors or methionine synthesis inhibitors are tested for their ability to reduce homocysteine levels in animal models, including humans.

For the treatment of infectious diseases such as *Pneumocystis carnii*, methods such as those described by WO 2005/000239 are used. Methods for modulating virulence have also been described (WO 2000/074686). Other infectious disease treatments use methods known to those skilled in the art. Imaging studies follow the methods described by Deng et al., 2011 S-11C-methyl-L-cysteine: a new amino acid PET tracer for cancer imaging. J Nucl Med. 2011 February; 52(2):287-93. Epub 2011 Jan. 13.

7. EXAMPLES

In order to more fully illustrate the invention, the following examples are provided.

7.1. Example

Identification of active microcin methionine analogue or methionine synthesis inhibitors.

In order to further assess new microcin producing strains or those strains identified above, methods known to those skilled in the arts are employed. Briefly, the culture supernatant is separated from the bacteria by centrifugation, followed by filtration through a sterile 0.22 micrometer filter.

The effect of the microcins, methionine analogues or methionine synthesis inhibitors on in vitro cytotoxicity toward cancer cells is determined using standard cell culture techniques and cytotoxicity assays such as MTT (3-(4,5-Dimethylthiazol-2-yl)-2,5-diphenyltetrazolium bromide, a tetrazol; Mosmann 1983; J. Immunol Methods 65:55-63). The contribution of the microcins, methionine analogues or methionine synthesis inhibitors and cytotoxic agents or methioninase are determined individually and in combination. Combination effects, including antagonism, additivity or synergy may determined using the median effect analysis (Chou and Talaly 1981 Eur. J. Biochem. 115: 207-216) or other standard methods (White et al., 1996, Antimicrobial Agents and Chemotherapy 40: 1914-1918; Brenner, 2002, Annals of Oncology 13: 1697-1698; Berenbaum MC. 1989. What is synergy? Pharmacol Rev. 41(2): 93-141; Greco WR, Bravo G, Parsons JC. 1995. The search for synergy: a critical review from a response surface perspective. Pharmacol Rev. 47(2): 331-85); Zhao et al., 2004, Evaluation of Combination Chemotherpy, Clin Cancer Res 10: 7994-8004; Loewe and Muischnek, 1926. Effect of combinations: mathematical basis of the problem, Arch. Exp. Pathol. Pharmakol. 114: 313-326). The assay may also be used to determine synergy, additivity or antagonism of two or more bacterial methionine analogue microcins, or in combination with methioninase. The assay may also be used to determine synergy, additivity or antagonism a bacterial methionine analogue microcins together with microtubule depolymerizing agents (vincristine, vinorelbine, vinblatine and mebendazole) conventional small molecule cytotoxin (e.g., cisplatin, doxorubicin, irinotecan, paclitaxel; Chu and DeVita, 2010, Physicians' Cancer Chemotherapy Handbook, Jones and Bartlett), targeted therapeutic (e.g., imatinib, irissa, cetuximab), proteosome inhibitors (e.g., bortezomib), mTOR inhibitors or PARP inhibitors.

7.2. Example

Purification of microcin methionine analogue or methionine synthesis inhibitors.

Active microcin methionine analogue or methionine synthesis inhibitors can be further purified as described by Morin et al., 2011 (Antimicrobial Agents and Chemotherapy, 55: 997-1007), wherein purified microcin is obtained by solid-phase extraction on Sep-Pak plus environmental C18 cartridges, followed by concentration under vacuum and then by subjecting it to a separation by C8 Reverse Phase-HPLC. A final C8 reverse phase column is used and eluted with 50% (vol/vol) acetonitrile—0.1% (vol/vol) trifluoroacetate. After the separation antimicrobial activity is determined. The material may be dried under vacuumed and redissolved in a pharmaceutically acceptable carrier for additional assays inclining dose-ranging tolerability studies and antitumor efficacy.

7.3. Example

Dose-Ranging Tolerability Study

In order to assess the potency of a substantially purified methionine analogue microcin, a standard dose-ranging study is performed. Dose escalation begins at 1 mg/kg Q2Dx3 X2, given IV and followed for 2 weeks post administration. The general appearance and body weight are used as in-life indicators of general health, and organ weights used at the end of the study period. Deviations of less than 15% of normal are deemed sufficiently safe to proceed to higher doses. If, at 1 mg/kg Q2Dx3 X2 is shown to be toxic, the dose will be lowered by 50% until a safe dose is determined. If, at 1 mg/kg Q2Dx3 X2 is shown to be non-toxic, the dose will be increased by 50% until a safe, maximally tolerated dose is determined.

7.4. Example

Anti-Tumor Effect(s) of Microcin Methionine Analogues

A tumor type known to be sensitive to methionine may be selected, such as the human lung cancer cell line H460 (Miki et al., 2000, Cancer Gene Therapy 7: 332-338). Tumor cells are implanted into nude mice and allowed to progress until palpable. Following palpation, all tumors are measured by calipers 3x/week. Animals, 6 per group, are placed into 3 groups:
1) control, saline treatment,
2) 50% MTD dose of methionine analogue microcin, and
3) MTD dose of methionine analogue microcin.

Tumor volume is evaluated over time. A significant retardation in tumor growth such that the treatment group is <50% of the untreated control group, or reduction in tumor volume considered the equivalent of one log cell kill.

In vivo studies (G. K. Schwartz (ed) 2005, Combination cancer therapy: Modulators and potentiators, Human Press, Totowa, N.J., 284 pp.; B. A. Teicher and P. A. Andrews (eds.) 2004, Anticancer drug development guide, Preclinical screening, clinical trials and approval, Second Edition, Humana Press, Totowa, N.J., 450 p.; Teicher (ed.) 2002, Tumor models in cancer research, Human Press, Totowa, N.J., 690 p) may also be performed with antiangiogenic inhibitors such as Avastin, combrettastatin, thalidomide.

In this description, several preferred embodiments were discussed. Persons skilled in the art will, undoubtedly, have other ideas as to how the compositions and methods described herein may be used. It is understood that this broad invention is not limited to the embodiments discussed herein. All references cited above are expressly incorporated herein by reference in their entirety.

What is claimed is:

1. A method of treating an animal, comprising orally, transdermally or transmucosally administering an effective dose of at least one substantially purified pharmaceutically acceptable microcin methionine analogue or microcin methionine synthesis inhibitor, except for microcin 15m or a microcin from E. coli LP15, having tumor growth inhibitory activity to a human or an animal having a neoplasm, to thereby treat the neoplasm.

2. The method according the claim 1, further comprising coadministering the pharmaceutically acceptable microcin methionine analogue or microcin methionine synthesis inhibitor in combination with a microtubule depolymerizing agent.

3. The method according to claim 2, wherein the microtubule inhibitory agent comprises at least one of vincristine, vinorelbine, vinblatine and mebendazol.

4. The method according the claim 1, further comprising coadministering the at least one pharmaceutically acceptable microcin methionine analogue or microcin methionine synthesis inhibitor in combination with methioninase.

5. The method according to claim 1, wherein the human or animal has a tumor comprising a neoplasia originating in a tissue selected from the group consisting of stomach, colon, rectum, liver, pancreas, lung, breast, cervix uteri, corpus uteri, ovary, prostate, testis, bladder, kidney, brain, central nervous system, head, neck, throat, or selected from the group consisting of Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney and lymphoma cancer.

6. The method according the claim 1, wherein the pharmaceutically acceptable microcin methionine analogue or microcin methionine synthesis inhibitor comprising a microcin which is at least one of (a) derived from *E. coli* LP 136, *E. coli* LP-93, D93, N-15, V517; (b) encoded by at least one plasmid selected from the group consisting of plasmid pCP101, pCP102, pCP103, pCP104, pCP105, pCP106, and pVA517C.

7. A method of treating a human or an animal, comprising:
determining a presence of a neoplastic disease;
orally, transdermally or transmucosally administering a regimen of effective doses of a pharmaceutically acceptable composition comprising at least one microcin methionine analogues or microcin methionine synthesis inhibitors, except for microcin 15m or a microcin from *E. coli* LP15, to the human or animal determines to have the presence of the neoplastic disease, over a sufficient time to achieve an effective treatment of the neoplastic disease.

8. The method according to claim 7, further comprising monitoring the treatment by performing at least one laboratory test to determine at least a neoplasm size, and altering the administration of the regimen of effective doses in dependence on the at least one laboratory test.

9. The method according to claim 7, further comprising providing the regimen of effective doses as a series of pharmaceutically acceptable unit dosage forms.

10. The method according to claim 7, further comprising coadministering a microtubule depolymerizing agent.

11. The method according to claim 7, further comprising concurrently administering methioninase during the regimen of effective doses.

12. The method according the claim 7, wherein the pharmaceutically acceptable composition comprises a purified microcin methionine analog.

13. The method according to claim 7, wherein the pharmaceutically acceptable composition comprises a purified tRNA microcin methionine synthesis inhibitor.

14. Amended in its entirety to read: The method according the claim 7, wherein the pharmaceutically acceptable microcin methionine analogue or microcin methionine synthesis inhibitor comprising a microcin which is at least one of (a) derived from *E. coli* LP 136, *E. coli* LP-93, D93, N-15, V517; (b) encoded by at least one plasmid selected from the group consisting of plasmid pCP101, pCP102, pCP103, pCP104, pCP105, pCP106, and pVA517C.

15. Amended in its entirety to read: A pharmaceutical composition for oral, transdermal or transmucosal administration to a human or animal, comprising at least one pharmaceutically acceptable agent selected from the group consisting of a substantially purified microcin methionine analogue and a substantially purified tRNA microcin methioinine synthesis inhibitor, except for microcin 15m or a microcin from *E. coli* LP15, in unit dose form.

16. The pharmaceutical composition according to claim 15, further comprising at least one pharmaceutically acceptable excipient, additive or carrier.

17. The pharmaceutical composition according to claim 15, wherein the unit dosage form comprises an oral unit dosage form.

18. The pharmaceutical composition according to claim 15, wherein the unit dosage form comprises a dosage form suitable for administration by application to a mucous membrane.

19. The pharmaceutical composition according to claim 15, wherein the unit dosage form comprises a dosage form suitable for transdermal administration.

20. Amended in its entirety to read: The pharmaceutical composition according the claim 15, wherein the pharmaceutically acceptable agent comprises a microcin which is at least one of (a) derived from *E. coli* LP 136, *E. coli* LP-93, D93, N-15, V517; (b) encoded by at least one plasmid selected from the group consisting of plasmid pCP101, pCP102, pCP103, pCP104, pCP105, pCP106, and pVA517C.

* * * * *